United States Patent [19]

Lissot et al.

[11] 3,985,134

[45] Oct. 12, 1976

[54] EXTRACORPOREAL BLOOD CIRCUIT

[75] Inventors: Jean Lissot, Brie Comte Robert; Andre Sausse, Sceaux, both of France

[73] Assignee: Rhone-Poulenc S.A., Paris, France

[22] Filed: Nov. 25, 1974

[21] Appl. No.: 527,041

[30] Foreign Application Priority Data
Nov. 26, 1973 France............................... 73.42007
Oct. 9, 1974 France............................... 74.33982

[52] U.S. Cl. ....................... 128/214 R; 128/DIG. 3; 128/214 F; 210/321 B; 251/7
[51] Int. Cl.² .......................................... A61M 1/03
[58] Field of Search......... 128/214 R, 214 B, 214 E, 128/214 F, 214.2, 274, DIG. 3; 251/4, 7, 9; 210/89, 90, 321 K

[56] References Cited
UNITED STATES PATENTS

| | | | |
|---|---|---|---|
| 2,313,550 | 3/1943 | Huber..................................... | 251/7 |
| 2,366,424 | 1/1945 | Perry ..................................... | 251/9 X |
| 2,695,932 | 1/1953 | Salisbury........................... | 128/214.2 |
| 3,550,619 | 12/1970 | Halasz et al. ....................... | 251/7 X |
| 3,756,234 | 9/1973 | Kopp................................... | 128/214 R |
| 3,791,767 | 2/1974 | Shill ................................... | 128/214 R X |
| 3,811,800 | 5/1974 | Shill ................................... | 128/214 B X |
| 3,830,234 | 8/1974 | Kopp................................... | 128/214 E |
| 3,848,592 | 11/1974 | Willock............................... | 128/214 R |

Primary Examiner—Dalton L. Truluck
Attorney, Agent, or Firm—Stevens, Davis, Miller & Mosher

[57] ABSTRACT

An extracorporeal blood circuit including a haemodialyser and a pump for pumping blood to and from the haemodialyser, and a single needle for the passage of the blood to and from the body. The single needle is connected to the stem of a Y-shaped coupling, the first branch of which is connected to an inlet pipeline for the pump, an intermediate pipeline connecting the pump to the inlet of the haemodialyser, the outlet of which is connected to the second branch of the Y, a bubble trap being included in the outlet pipeline. A device is provided which seals the inlet and outlet pipelines intermittently and this is driven in a cyclic manner at a predetermined frequency. The haemodialyser and/or the pump and/or the intermediate or outlet pipeline has a variable internal volume which is sensitive to the variations in the differential pressure instantaneously existing between its interior and atmosphere. This may be effected by making some of these elements resilient, so that they can expand when the pressure increases. By this means it is unnecessary to provide pressure detectors which control the alternate occlusion of the pipelines. This substantially reduces the cost of manufacture and running the blood circuit.

8 Claims, 3 Drawing Figures

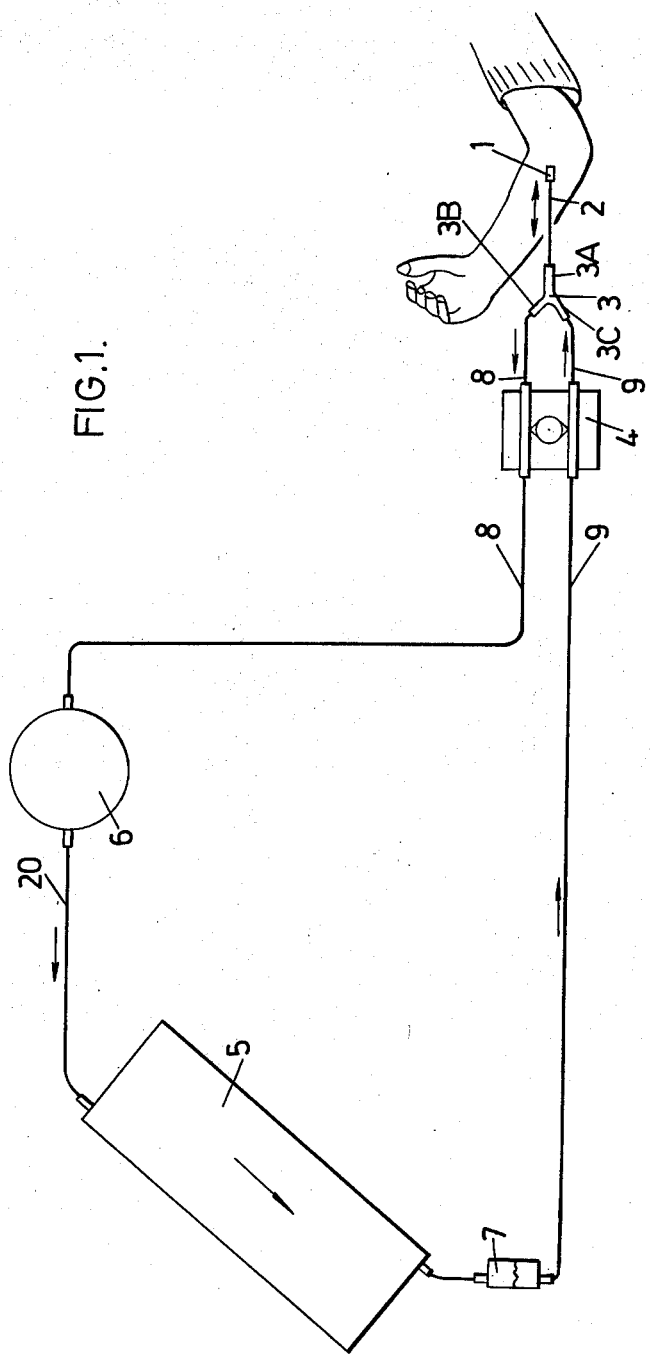

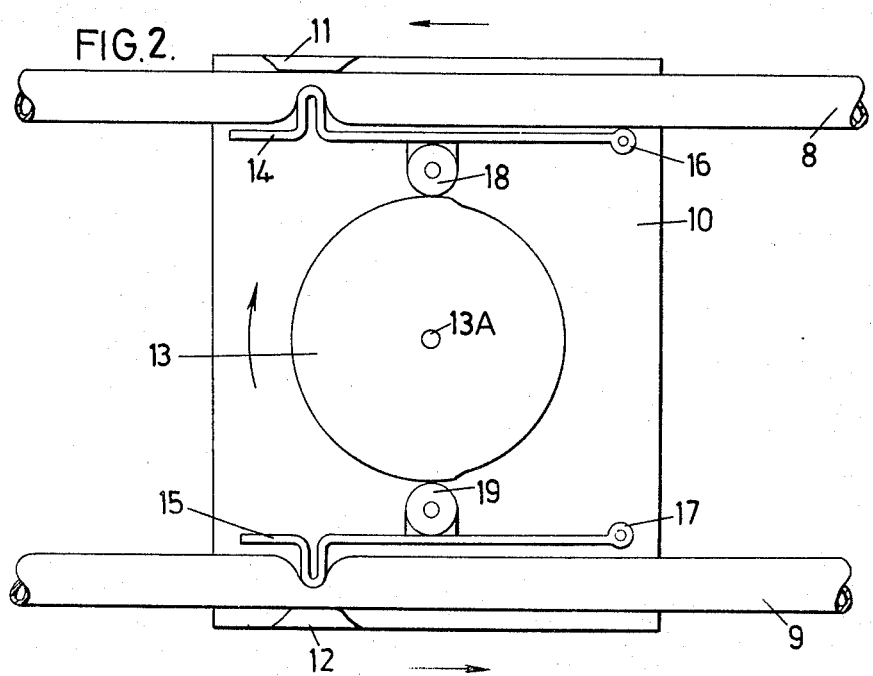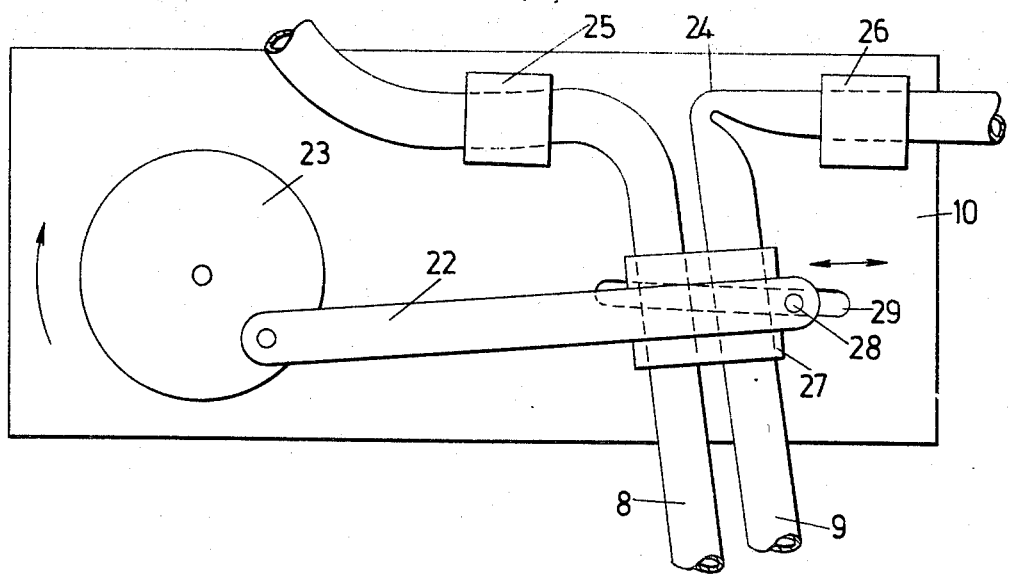

EXTRACORPOREAL BLOOD CIRCUIT

The present invention relates to extracorporeal blood circuits for supplying a haemodialyser from a single needle through which the blood to be purified and the purified blood pass alternately.

Such a circuit is described in detail in the article "Single needle dialysis" by K. F. Kopp, G. F. Guth and W. J. Koff published in Volume XVIII of Trans. Amer. Soc. Artif. Int. Organs 1972. The circuit described requires the use of pressure detectors connected to a monitor which is specially designed to control the alternate occlusion of the pipelines for supplying blood to and removing it from the haemodialyser. These pressure detectors are delicate components involving the use of relatively complex and expensive equipment.

According to the present invention we provide an extracorporeal blood circuit comprising a haemodialyser, a continuously operable peristaltic pump of a type which exerts at most only a slight haemolysing effect, a hollow needle which can be introduced into a patient's blood vessel, a Y-shaped coupling having a stem connected to said hollow needle and first and second branches, an inlet pipeline connecting the first branch to the inlet of the pump, an intermediate pipeline connecting the outlet of the pump to the inlet of the haemodialyser, an outlet pipeline connecting the outlet of the haemodialyser to the second branch of the Y-shaped coupling, a bubble trap in said outlet pipeline, a device which seals the inlet and outlet pipelines intermittently, and means to drive said device in cyclic manner at a predetermined frequency, at least one of the haemodialyser, the pump, the intermediate pipeline and the outlet pipeline having a variable internal volume which is sensitive to the variations in the differential pressure instantaneously existing between its interior and atmosphere.

Such a circuit may be constructed so as to be simple, reliable and economical and one does not require the use of pressure detectors. It is also possible substantially to reduce the rate at which blood is recirculated inside the haemodialyser.

The internal volume may be made variable by any suitable means, for example, by the use of a piston in a cylinder, but it is preferably made variable by constructing the pump and/or the haemodialyser and/or the pipelines and/or their accessories with elastic walls.

In order that the present invention will be better understood, the following description is given, by way of example only, reference being made to the accompanying drawings, in which:

FIG. 1 is a schematical view of one embodiment of circuit according to the invention;

FIG. 2 is an enlarged view in elevation of the device for sealing the pipelines of the circuit of FIG. 1; and FIG. 3 is a similar view of a different embodiment of such a device.

Referring to FIG. 1, the circuit according to the invention comprises a hollow needle 1 of known type for removing blood from a vessel of a patient, for example a vein in the forearm. The needle 1 is connected via a section of pipeline 2 of short length (a few centimeters) to the stem 3A of a Y-shaped coupling 3 of known type. The two branches 3B and 3C of the Y are each connected to a device 4 for effecting the intermittent sealing of an inlet pipeline 8 and an outlet pipeline 9 arranged in parallel for supplying blood to and removing it from a haemodialyser 5.

The inlet pipeline 8 extends from the first branch 3B of the Y-shaped coupling 3 to the inlet of a pump 6, which is of a type which exerts only a slight haemolysing effect. The outlet of the pump is connected by an intermediate pipeline 20 to the inlet of the haemodialyser 5. The outlet pipeline 9 extends from the outlet of the haemodialyser 5 to the Y-shaped coupling via a bubble trap 7 of known type and the device 4. The pump 6 and the device 4 for sealing the inlet and outlet pipelines intermittently are connected by known means (speed-reducing or speed-varying devices, coupling sleeves and the like) to drive components of type which are in themselves known and are not represented and are driven at speeds which are generally constant and may be fixed or adjustable. The direction in which the blood circulates is indicated by arrows.

This circuit functions in the following way. Blood is removed from the patient via the needle 1 and is conveyed by the pump 6 to the haemodialyser 5 where it is purified. After having passed through the bubble trap 7 where it is degassed if necessary, it is re-injected into the patient through the needle which was employed to remove it. To achieve this, the device 4 substantially alternately seals the pipelines for supplying the blood to and removing it from the haemodialyser.

According to the prior art, blood ceases to be introduced into the haemodialyser by sealing the supply pipeline as soon as the pressure of the blood reaches the maximum value permissible at the outlet of the pump 6 and this requires a variable period of time. A portion of the purified blood is then removed during a predetermined period of time, and then the cycle begins again.

According to the invention, it is the frequency of the entire cycle, comprising successively the supply of blood to, followed by the removal of blood, from, the haemodialyser, which is predetermined, and this applies independently of the pressure of blood inside the circuit. It has in fact been found that under the conditions which are specified below, the variations in pressure of the blood inside the pump, the haemodialyser, the connecting pipelines and, where appropriate, their accessories generate variations in the volume with which the blood is provided by these components, these variations in volume in their turn restricting the rise in pressure of the blood to a completely acceptable level, that is to say a level which removes practically any danger of rupture of the walls, including the membranes, in contact with the blood.

The conditions to be fulfilled relate to the ability of at least one of the abovementioned components to undergo deformation reversibly and generally (and preferably) elastically, so as to provide the blood with an internal volume which varies as a function of a variation in the pressure of the blood. The variable volume can reach a maximum permissible value at least equal to the volume of blood displaced during each cycle.

Thus the pump 6 preferably possesses an element consisting of a flexible tube which provides the blood with an internal volume (between two wheels or between two valves) which can vary and which is sensitive to variations in the pressure exerted on its walls. It is found that, no matter what the drive speed of such a pump may be, its output can decrease until it becomes zero, either if the pressure at the outlet of the pump increases, or if the pressure at the inlet of the pump decreases.

The pumps used in extracorporeal blood circulation do not necessarily possess such properties. In order to carry out the present invention, it is possible preferably to use, as the pump, either peristaltic pumps described, for example, in French Pat. Nos. 1,529,860 and 2,063,677, or pumps with a tubular membrane and a valve (also called ventricular pumps) possessing an inlet valve which is automatic or preferably controlled and an output valve which is controlled and which can be of the same type as the inlet valve, for example the pumps according to French Pat. No. 72/07,863. It is known that it is easy to adjust the pressure of the drive fluid of such pumps and consequently their output pressure and their reduction in pressure at intake. In the case of the so-called ventricular pumps, the internal volume with which the blood is provided is sensitive to the differential pressure which is exerted on the wall of the tube; the differential pressure is the difference between the pressures which are exerted at any instant on the inside and on the outside of the tube.

The pump of preferential type enables the device according to the invention to function with very great safety, because it automatically prevents any accident, for example if the needle 1 were to become clogged or the device 4 for effecting intermittent sealing operations were to remain blocked, the outlet pipeline would remain closed.

It is also possible to use any known type, which may or may not be preferential, of pump which exerts only a slight haemolysing effect, for example a peristaltic pump connected to a pipeline for introducing blood and to a pipeline for passing blood through the haemodialyser which provides the blood with an internal volume which preferably varies elastically and is sensitive to variations in the differential pressure exerted on the walls of the pipelines.

These pipelines generally consist of flexible tubes which can have a circular, elliptical or fusiform cross-section at rest. When a flexible tube which is at rest provides the blood with a circular cross-section through which it can pass, it increases in diameter under the effect of an increase in internal pressure by elastic elongation of the wall, that is to say by expansion of the tube, and returns to its original size when the internal pressure ceases. When the cross-section of the tube at rest is non-circular, it can vary both under the effect of a decrease in pressure (upstream from the pump 6) and under the effect of an internal increase in pressure (downstream from the pump 6), due to the walls of the tube bending. It is preferred to use tubes which alter in cross-section due to wall bending because they make it possible to obtain a large variation in volume for a small variation in pressure. Amongst the latter tubes, those which change in cross-section by elastic or resilient bending of their wall are preferred. In practice, the flexible tubes usually employed in extracorporeal circulation, for example those made of silicone elastomers, are very suitable, obviously insofar as they possess the necessary ability to change their internal volume as a function of the pressure.

It is also possible to use, in conjunction either with a pump of preferential type of with an intake pipeline, the internal volume of which is sensitive to variations in pressure, haemodialysers which in themselves provide the blood with a variable volume sensitive to variations in the differential pressure exerted on their walls. In practice, most of the known haemodialysers possess such a property.

Of course, it is possible to combine the preferential elements with one another. If desired, it is also possible to connect accessories, such as flexible pouches with elastic walls (not represented), to the supply pipeline, it being possible for these accessories firstly to damp sudden variations in the pressure of the blood and secondly to increase the capacity of this pipeline in relation to the variations in volume with which the blood is provided.

FIG. 2 represents one embodiment of a device for effecting the intermittent sealing of the two pipelines connecting the patient to the haemodialyser.

In this device the two flexible tubes, that is the inlet tube 8 and the outlet tube 9, are substantially parallel and are held by a support plate 10 at two opposite bearing zones 11 and 12. Between the two tubes, a cam 13 driven, at a predetermined speed which may be fixed or adjustable, by a shaft 13A, and controls two symmetrical small rods 14 and 15. These small rods can pivot at one end about axles 16 and 17; they carry cam follower wheels 18 and 19 which rotate in contact with the cam 13 and keep the small rods pressed against the tubes 8 and 9. Near their free end, the small rods each have a protruding and rounded shape which enables them to compress the flexible tubes 8 and 9 on a level with the opposite bearing zones 11 and 12, until they seal the tubes completely, without damaging them and practically without haemolysing the blood. Advantageously, the small rods are elastic and consist, for example, of leaf springs, in order to achieve satisfactory sealing of the tubes 8 and 9, no matter what the tolerances to which they are manufactured may be.

The cam 13 forces the small rods 14 and 15 to seal the flexible tubes 8 and 9 substantially alternately. It is clear that the period of time during which the pump 6 sends blood to the haemodialyser 5 whilst the device 4 seals the pipeline for purified blood is limited. In fact, the volume of blood displaced by the pump during this period of time is less than or at most equal to the maximum permissible variation in the internal volume of the various components of the output circuit of the pump, the walls of which are sensitive to variations in pressure. Likewise, the period of time during which the purified blood flows is also limited in order to avoid subjecting the blood to too great a reduction in pressure in the intake circuit of the pump. Consequently it is advisable to choose a cyclic operation for the sealing device 4, the frequency of which is generally between 10 and 50 cycles per minute and preferably between 20 and 40 cycles per minute. The duration of the cycle will be the longer, the more flexible are the components of the circuit (pump, pipelines, haemodialyser, bubble trap and the like) and the more they will tolerate an increase and/or decrease in volume under the effect of a variation in pressure. The duration of the cycle will obviously be shorter in the opposite case. The period of time for which the haemodialyser is supplied with blood to be purified is substantially equal to the period of time during which the purified blood is removed.

Advantageously, the profile of the cam 13 is determined, as represented in FIG. 2, so as to make it possible to seal both the tubes simultaneously for a short period of time. Because of this particular arrangement, the re-circulation through the haemodialyser of blood which has already been purified is considerably reduced, since only the blood present in the common section of pipeline 2 or very small volume can be recycled.

In fact, according to the prior art, the two pipelines are not completely closed simultaneously and so, in each cycle, during the period of closing or opening the pipelines, a portion of the purified blood is sucked in by the pump 6 and returned directly to the haemodialyser. This results in a lowering of the efficiency of the latter, which is compensated for only by prolonging the duration of the treatment. The latter can be as much as 20 to 30% or even more of the duration of the treatment carried out with two separate needles, all other conditions being equal.

Thus the present invention enables the technique of single needle haemodialysis to derive benefit from all its advantages whilst practically eliminating its main disadvantages.

The following example will make the characteristics and the advantages of the circuit according to the invention clear.

EXAMPLE

An extracorporeal circuit comprising the following elements is used:

A needle of internal diameter 2 mm and length 30 mm, a Y-shaped coupling, the branches of which have an internal diameter of 4 mm and a length of 10 mm, a rotary peristaltic pump with three wheels pressing a tube made of silicone elastomer, $\phi$ 10 – 14 mm, according to a nominal circle of diameter 114 mm. This pump is of the type described in the French Pat. published under No. 2,063,677, a haemodialyser sold by the Medical Engineering Department of Messrs. RHONE-POULENC, of the type RP No. 5. It comprises 30 membranes with a useful unit surface area of 370 cm$^2$, a bubble trap consisting of a tube made of silicone elastomer of volume 20 cm$^3$, a device possessing a cam as represented in FIG. 2, and connecting pipelines made of silicone elastomer of $\phi$ 5–8 mm.

A single needle haemodialysis treatment is carried out using this equipment. To do this, after having connected the patient to the circuit thus formed, the pump is driven at a constant speed of 20 revolutions/minute and the cam is driven at a speed of 30 revolutions/minute. The flow rate of blood passing through the haemodialyser is 200 ml/minute and the flow rate of recycled blood is only 10 ml/minute.

Of course, the present invention is not limited only to the embodiments described and comprises any different embodiments lying within the scope of those skilled in the art. For example, the device 4 for effecting intermittent sealing operations can comprise an eccentric element instead of a cam, or any combination of equivalent means, for example a rod 22 and crankshaft 23 system driving the combination of the two flexible pipelines 8 and 9, as represented in FIG. 3, thus inducing alternate kinks, e.g. as illustrated at 24 in pipeline 9, the kinks sealing the respective pipeline. In this construction the pipelines are held on the support plate 10 by clamps 25 and 26, while the lower parts of the pipelines are reciprocated by a collar 27 mounted on rod 22, which carries a pin 28 sliding in guide slot 29 in the plate 10.

We claim:
1. An extracorporeal blood circuit comprising, in combination:
   a. a haemodialyser having an inlet and an outlet;
   b. a continuously operable pump of a type which exerts at most only a slight haemolysing effect and having an inlet and an outlet;
   c. a hollow needle which can be introduced into a patient's blood vessel;
   d. a Y-shaped coupling having a stem connected to said hollow needle and first and second branches;
   e. an inlet pipeline connecting said first branch to the inlet of the pump;
   f. an intermediate pipeline connecting the outlet of the pump to the inlet of the haemodialyser;
   g. an outlet pipeline connecting the outlet of the haemodialyser to the second branch of the Y-shaped coupling;
   h. a bubble trap in said outlet pipeline;
   i. a device which seals the inlet and outlet pipelines intermittently, said device including means to seal both the pipelines simultaneously for an instant in the course of a cycle; and
   j. drive means which drive said device in a cyclic manner at a predetermined frequency;
at least one of the haemodialyser, the pump, the intermediate pipeline and the outlet pipeline having a variable internal volume which is sensitive to the variations in the differential pressure instantaneously existing between its interior and atmosphere.

2. An extracorporeal blood circuit as claimed in claim 1, wherein the walls of at least one of the haemodialyser, the pump, the intermediate pipeline and the outlet pipeline are resilient.

3. An extracorporeal blood circuit as claimed in claim 1, wherein the pump is a statorless peristaltic pump.

4. An extracorporeal blood circuit as claimed in claim 1, wherein the drive means are operable whereby the device which seals the inlet and outlet pipelines intermittently operates in a cyclic manner at a frequency of between 10 and 50 cycles per minute.

5. An extracorporeal blood circuit as claimed in claim 1, wherein the device which seals the pipelines comprises a single cam.

6. An extracorporeal blood circuit as claimed in claim 5, and further comprising a fixed support against which said inlet and outlet pipelines bear and two symmetrical small rods each of which has a rounded end shape enabling them to seal the flexible pipelines against the support, said cam operating against said small rods.

7. An extracorporeal blood circuit as claimed in claim 6, wherein said small rods are resilient.

8. An extracorporeal blood circuit comprising, in combination:
   a. a haemodialyser having an inlet and an outlet;
   b. a pump of a type which exerts at most only a slightly haemolysing effect and having an inlet and an outlet;
   c. a hollow needle which can be introduced into a patient's blood vessel;
   d. a Y-shaped coupling having a stem connected to said hollow needle and first and second branches;
   e. an inlet pipeline connecting said first branch to the inlet of the pump;
   f. an intermediate pipeline connecting the outlet of the pump to the inlet of the haemodialyser;
   g. an outlet pipeline connecting the outlet of the haemodialyser to the branch of the Y-shaped coupling;
   h. a bubble trap in said outlet pipe;

i. a device which seals the inlet and outlet pipelines intermittently, said device including means to seal both the pipelines simultaneously for an instant in the course of a cycle; and j. drive means which drive said device in a cyclic manner at a predetermined frequency;

at least one of the haemodialyser, the pump, the intermediate pipeline and the outlet pipeline having a variable internal volume which is sensitive to the variations in the differential pressure instantaneously existing between its interior and atmosphere.

* * * * *